United States Patent
Kang et al.

(10) Patent No.: US 7,647,189 B2
(45) Date of Patent: Jan. 12, 2010

(54) METHOD AND DEVICE FOR INSPECTION OF DRUGS CONCEALED IN LIQUID ARTICLES

(75) Inventors: Kejun Kang, Beijing (CN); Zhiqiang Chen, Beijing (CN); Haifeng Hu, Beijing (CN); Yuanjing Li, Beijing (CN); Li Zhang, Beijing (CN); Yinong Liu, Beijing (CN); Xuewu Wang, Beijing (CN); Lijun Qiu, Beijing (CN); Hong Zhang, Beijing (CN)

(73) Assignees: Tsinghua University, Beijing (CN); Nuctech Company Limited, Beijing (CN)

( * ) Notice: Subject to any disclaimer, the term of this patent is extended or adjusted under 35 U.S.C. 154(b) by 0 days.

(21) Appl. No.: 12/078,981

(22) Filed: Apr. 9, 2008

(65) Prior Publication Data

US 2009/0006019 A1    Jan. 1, 2009

(30) Foreign Application Priority Data

Jun. 29, 2007    (CN) .................. 2007 1 0118145

(51) Int. Cl.
*G01N 31/00* (2006.01)
*G01N 37/00* (2006.01)

(52) U.S. Cl. .................. 702/25; 378/53; 378/88; 702/82

(58) Field of Classification Search .................. 702/22, 702/25, 30, 82; 378/53, 88; 340/568.1
See application file for complete search history.

(56) References Cited

U.S. PATENT DOCUMENTS

| 5,600,303 | A | * | 2/1997 | Husseiny et al. | ......... 340/568.1 |
| 5,692,029 | A | * | 11/1997 | Husseiny et al. | .............. 378/88 |
| 2005/0084063 | A1 | * | 4/2005 | Heismann et al. | .............. 378/53 |

* cited by examiner

*Primary Examiner*—John H Le
(74) *Attorney, Agent, or Firm*—Jacobson Holman PLLC

(57) ABSTRACT

A method and a device are provided for inspection of liquid articles to determine the presence of drugs concealed in the liquid articles without opening the outer packages. The method includes emitting radiation beams having a single energy to transmit through the liquid article; receiving the radiation beams transmitted through the liquid article to get multi-angle projection data; inversely operating the multi-angle projection data based on the uniformity of the liquid article to obtain an attribute value of the inspected liquid article; retrieving a reference attribute value in a pre-created database by using the identification information of the liquid article as an index, and calculating a difference between the calculated attribute value and the reference attribute value; and determining whether the difference is larger than a predefined threshold value. When the predefined threshold value is exceeded by the difference, it is concluded that there are drugs concealed in the liquid article and this result is output to a user for appropriate action.

20 Claims, 4 Drawing Sheets

METHOD AND DEVICE FOR INSPECTION OF DRUGS CONCEALED IN LIQUID ARTICLES

BACKGROUND OF THE INVENTION

1. Field of Invention

The present invention relates to the field of drug detection, and particularly, to a method and device for inspection of liquid articles at the place such as customhouse, which is capable of determining whether drugs such as cocaine are concealed in the liquid articles by single energy CT imaging of the liquid articles.

2. Description of Prior Art

It is a difficulty common to custom of individual countries to render drugs such as cocaine concealed in liquid articles. Currently, there are mainly two ways to address this difficulty, including destructive inspection method, e.g. sampling and analyzing method, and non-destructive method, e.g. particle inspection method.

The sampling and analyzing method is to unpack the liquid articles to sample and analyze them so as to determine whether there are drugs concealed in the liquid articles. However, the insurmountable disadvantage of the method is that the outer packages of the liquid articles need to be broken, so the method is not suitable for regular inspection of general passengers.

The particle inspection method is to detect and discriminate minute drugs residue on the packages in the case that the outer packages of the liquid articles are not opened. However, the limitation of the method is that it may be ineffective if the drugs carriers can reduce the residue on the outer packages by for example injecting the drugs into a sealed container.

Therefore, a technology is needed that can determine whether there are drugs concealed in the liquid articles without destroying the outer packages of the liquid articles.

SUMMARY OF THE INVENTION

In order to overcome the disadvantages in the existing technologies, it is an object of the invention to provide a method as well as a device for inspection of drugs concealed in liquid article using single energy rays, which can conduct a quick detection and draw a conclusion whether there are drugs concealed in the liquid articles, without destroying the outer packages of the liquid articles.

In an aspect of the invention, a method for inspection of drugs concealed in liquid articles is provided, comprising the following steps: emitting radiation beams to transmit through the liquid articles; receiving the radiation beams transmitting through the liquid articles to get multi-angle projection data; inversely operating the multi-angle projection data based on the uniformity of the liquid articles to obtain an attribute value of the inspected liquid articles; retrieving a reference attribute value in a database setup in advance by using the identification information of the liquid articles as an index, and calculating a difference between the calculated attribute value and the reference attribute value; and determining whether the difference is above a predefined threshold value; wherein it is concluded that there are drugs concealed in the liquid articles when the difference is determined to be larger than the predefined threshold value.

In another aspect of the invention, a device for inspection of drugs concealed in liquid articles is provided, comprising: a radiation source for emitting radiation beams to transmit through the liquid articles; a detection and collection appliance for receiving the radiation beams transmitting through the liquid articles to get multi-angle projection data; and a computer data processor including means for inversely operating the multi-angle projection data based on the uniformity of the liquid articles to obtain an attribute value of the inspected liquid articles; means for retrieving a reference attribute value in a database setup in advance by using the identification information of the liquid articles as an index, and calculating a difference between the calculated attribute value and the reference attribute value; and means for determining whether the difference is above a predefined threshold value; wherein it is concluded that there are drugs concealed in the liquid articles when the difference is determined to be larger than the predefined threshold value.

By means of the device and the method according to the present invention, it can be determined whether there are suspicious articles such as drugs (for example, cocaine etc.) concealed in liquid articles (for example, drink). Besides, it is convenient for users because the users can add types of the liquid articles according to specific applications.

BRIEF DESCRIPTION OF THE DRAWINGS

The features and advantages of the invention can be more obvious from the following detailed descriptions in connection with the accompanying drawings, in which.

DETAILED DESCRIPTION OF THE PREFERRED EMBODIMENTS

Figure 1:
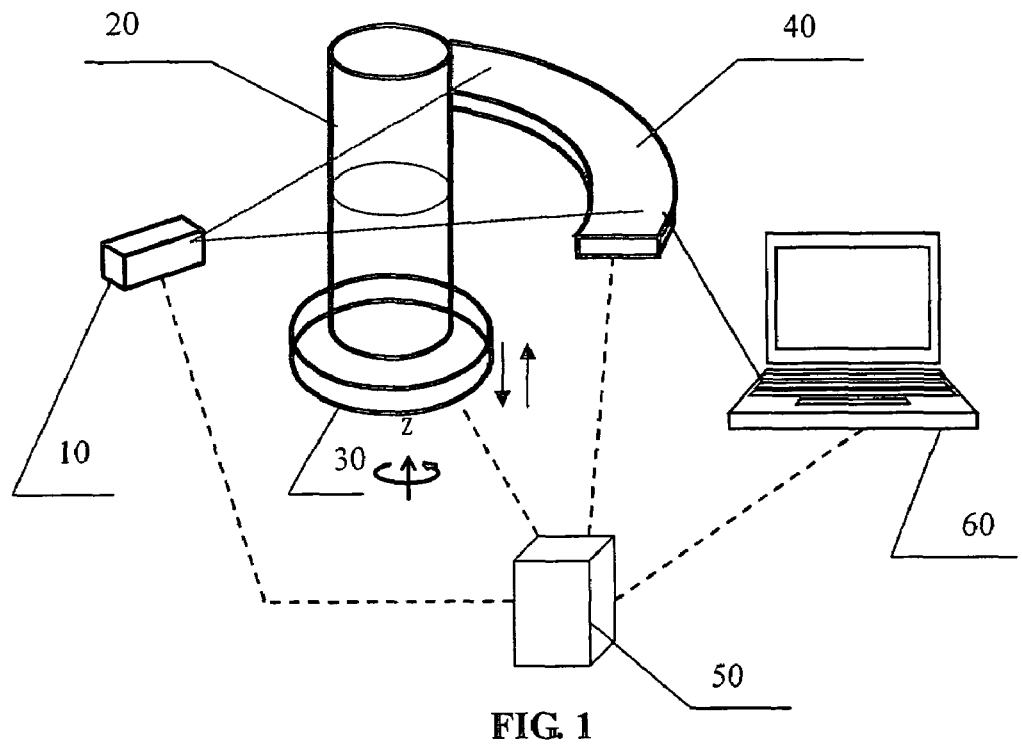
FIG. 1 is a schematic diagram of an inspection device according to an embodiment of the invention.

The preferred embodiment of the invention will now be described more fully hereinafter with reference to the accompanying drawings. In the drawings the same reference numerals are used for denoting the same or similar components that are shown in different figures.

FIG. 1 is a schematic diagram of an inspection device according to an embodiment of the invention.

As shown in FIG. 1, the inspection device according to an embodiment of the invention comprises a radiation source 10 for emitting radiations for detection, e.g. an X-ray machine or an isotope (X-ray or γ-ray source) source; a carrier mechanism 30, which carries the liquid articles under inspection 20, can rotate around axis Z thereof, and can ascend or descend to take the liquid articles 20 into the detection area, thereby the radiations emitted by the radiation source 10 can transmit through the liquid articles 20; a detection and collection appliance 40, an integrated module of a detector and a data collector, which is used to detect the radiations transmitted through the liquid articles 20 to acquire analog signals, and convert the analog signals into digital signals, and hence output the scanning data of the liquid articles 20; a scan controller 50, which controls each component of whole system so that they operate synchronously; and a computer data processor 60 for processing the data collected by the data collector and outputting detection results.

As shown in FIG. 1, the radiation source 10 is placed at one side of the carrier mechanism 30 carrying the liquid articles under inspection 20, while the detection and collection appliance 40 is placed at the other side of the carrier mechanism 30. The detection and collection appliance 40 comprises a detector and a data collector for acquiring the initial environmental information and the multi-angle projection data of the liquid articles 20. The data collector has a signal amplifying and formation circuit, which operates under (current) integration mode or pulses (counting) mode. The detection and collection appliance 40 has its data output cable connected with the computer data processor 60 to store the collected data therein.

Furthermore, the inspection device is also provided with a cylindrical article passage made of metal (not shown) provided on the carrier mechanism 30, which can shield X-rays from radiating outside. The liquid article under inspection is placed in the article passage.

Figure 2:
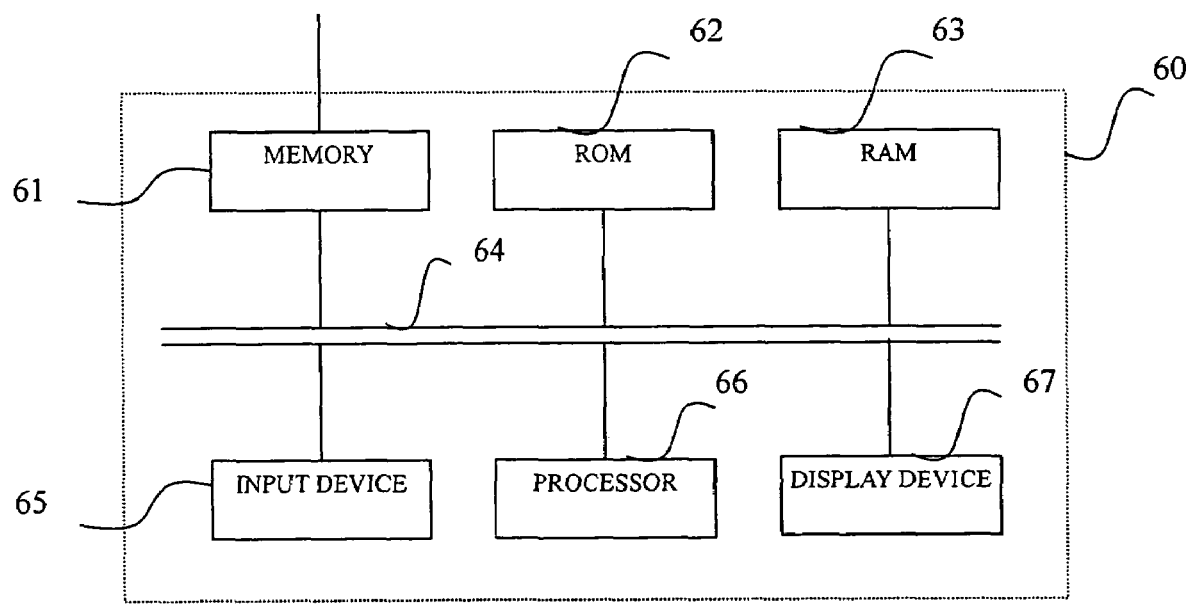
FIG. 2 shows a structure diagram of the computer data processor in the inspection device of FIG. 1.

FIG. 2 shows a structure diagram of the computer data processor 60 of FIG. 1. As shown in FIG. 2, the data collected by the data collector are stored in the memory 61. The configuration data and programs of the computer data processor are stored in the ROM (Read Only Memory) 62. The RAM (Random Access Memory) 63 is used for temporarily storing various data during the operating procedure of the processor 66. Besides, computer programs and a pre-created database are also stored in the memory 61 for data processing. The database stores various relevant parameters of known liquid articles, such as names, classes, physical attributes of the liquid articles and etc, to compare with the attribute values (such as CT values) of the liquid articles 20 computed by the processor 66. There is an internal bus 64 that connects the memory 61, the ROM 62, the RAM 63, the input device 65, the processor 66 and the display device 67 together.

After the user inputs operation commands through the input device 65 such as keyboards and mouse, the instruction code of the computer programs will instruct the processor 66 to perform predetermined data processing algorithm. After the data processing results are obtained, they will be displayed on the display device 67 such as LCD, or redirected in the form of a hard copy.

In general, the physical attribute of the liquid articles will change after there are drugs concealed therein. Consequently, it can be concluded whether there are drugs concealed in the liquid articles by determining the difference between a certain physical attribute of the liquid articles under inspection with the physical attribute of normal liquid articles.

According to an embodiment of the present invention, firstly an average attenuation coefficient of the liquid articles under inspection is calculated, and then it is converted into a CT value of the attenuation coefficient in relation to that of water. Afterward, the CT value actually measured is compared with a CT value of a corresponding type of liquid articles in a database setup in advance. It can be concluded that the liquid articles may have drugs concealed therein when the difference therebetween is larger than a predefined threshold value.

According to the embodiment of the present invention, an average attenuation coefficient of the liquid articles under inspection is calculated at first, and then it is converted into a CT value of the attenuation coefficient in relation to that of water according to the following formula:

$$CT = \frac{\mu_{CALCULATIONE} - \mu_{WATER}}{\mu_{WATER}} \times 1000 \qquad (1)$$

Wherein $\mu_{WATER}$ denotes the linear attenuation coefficient of water, and $\mu_{CALCULATION}$ denotes the measured linear attenuation coefficient of the scanned article. According to the above formula (1), the attenuation coefficients of all liquid articles can be converted into those in relation to water. From the above formula, it can be seen that the relative attenuation coefficient of water is 0.

As an alternative, similar operations can be conducted directly on the calculated average linear attenuation coefficients. For example, the difference between the calculated linear attenuation coefficient and a reference value, and the difference is compared with a predefined threshold value to determine whether there are drugs concealed in the liquid articles.

Figure 3:
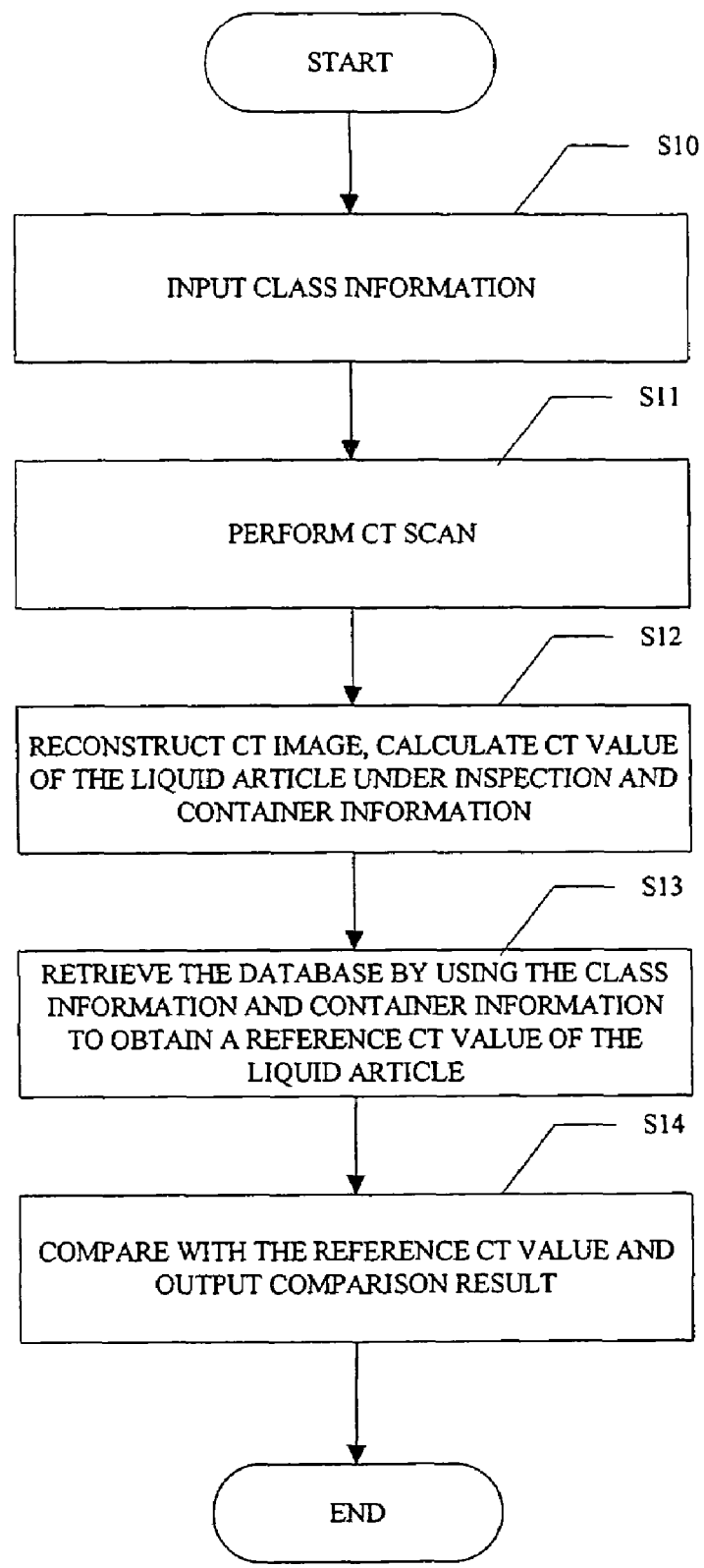
FIG. 3 shows a detailed flow chart of an inspection method for drugs concealed in liquid articles according to an embodiment of the invention.

FIG. 3 shows the flow chart of an inspection method according to an embodiment of the invention.

As shown in FIG. 3, at step S10, an operator get identification information of the liquid articles provided from the carrier of the liquid articles, or from outer packages of the liquid articles. The liquid articles are, e.g. a bottle of 40% rum. Here, the operator can input apriori information of the liquid article: distilled alcohol→rum→40%. Thereafter, the liquid articles under inspection 20 are placed on the carrier mechanism 30.

According to an embodiment of the present invention, when an operator sends out the command of starting a scan, at step S11, the scan controller 50 controls the radiation source 10 to emit radiations, and controls the carrier mechanism 30 to ascend and descend so as to enter the detection area constituted by the X-ray source 10 and the detector. At the same time, radiation beams are emitted from the radiation source 10 and transmit through the liquid articles 20. The scan controller 50 controls the detection and collection appliance 40 to receive the radiations transmitted through the liquid articles 20, to acquire initial environmental information of the liquid articles, such as the background information of the detector and the geometry boundary information, etc. The geometry boundary information can be obtained by the X-ray radiographic technique or by X-ray scan imaging technology. The X-ray scan imaging technology can adopt translating mode, rotating mode or spiral mode.

Besides, in the above procedures, the obtained initial environmental information of the liquid articles under inspection 20 contains the size of package, the material of package, the volume ratio of package to liquid articles, and so on. These information and attenuation coefficients or relative attenuation coefficients of various liquid articles can be pre-classified by using neural network recognition algorithm to form a database. In the real detection procedure, the detection of the liquid articles 20 is implemented by calculating the difference between the measured classified attributes and the classified attributes in the database and comparing the difference with a predefined threshold value.

Thereafter, at step S12, the carrier mechanism 30 rotates under the control of the scan controller 50. When the carrier mechanism 30 reaches the first angle, radiations will be emitted from the radiation source 10 to transmit through the liquid articles under inspection 20. The detection and collection appliance 40 receives the transmitted radiations to obtain the projection data of the first angle, which is denoted as a 1×N dimensional vector $g_1$ and stored in the memory 61 of the computer data processor 60, wherein N is the number of the detection units of one row in the detector.

The carrier mechanism 30 continues rotating under the control of the scan controller 50. When the carrier mechanism 30 reaches the second angle, radiations will be emitted from the radiation source 10 to transmit through the liquid article 20. The detection and collection appliance 40 receives the transmitted radiations to obtain the projection data of the second angle, which is denoted as 1×N dimensional vector $g_2$ and stored in the memory 61 of the computer data processor 60.

The above steps are repeated in this manner. The carrier mechanism 30 continues rotating under the control of the scan controller 50. When the carrier mechanism 30 reaches the $M^{th}$ angle, the projection data for $M^{th}$ angle is obtained, which is denoted as 1×N dimensional vector $g_M$ and stored in the memory 61 of the computer data processor 60. After the above scan procedure, the multi-angle projection data of the liquid articles 20 is obtained, which is denoted as an M×N dimensional vector g. Thereby, the multi-angle projection data of the liquid article under inspection 20 can be sequentially acquired for one slice.

Herein, in order to increase multi-angle projection data, the amount of angle projection can be increased during the scanning, or the detector is mounted with an offset of ¼ size of one detection unit of the detector.

Suppose that the linear attenuating coefficient of the liquid article under inspection 20 is expressed as an I-dimensional vector f, wherein I denotes the dimension of discretized pixels of the liquid article. Based on the interaction between radiations such as X-ray and substance, according to the Bill's Law, we can get:

$$g_1 = \exp(-H_1 f) \quad (2)$$
$$g_2 = \exp(-H_2 f)$$
$$\ldots \ldots$$
$$g_M = \exp(-H_M f)$$

wherein the $H_1, \ldots, H_M$ each represents an N×I system matrix, whose element $H_{nj}$ reflects the contribution of the discrete pixel j in the object image under the corresponding angle, to the signal collected by the $n_{th}$ detector. $H_1 \ldots H_M$ each is a single sparse matrix, which is determined by practical design of the scanning system. For example, these matrices can be determined by pre-computing and then being stored in the memory 61, or through a real time computation according to the temporal system parameters. Thus, the linear attenuating coefficient information of the liquid articles can be obtained through the inverse operation with regard to the formula (2).

The inverse operation is an inverse process of normal operation. The process of normal operation is that the original signal emitted by radiation source attenuates when transmitting through the liquid articles 20 and the detector receives the attenuated radiation signal. Accordingly, an inverse operation is to compute the information of radiation attenuation by the liquid articles on the basis of the signal received by the detector.

However, during the detection procedure of liquid articles, because the inverse operation is an ill-conditioned problem, other information needs to be incorporated, e.g. the geometry boundary information of the liquid articles under inspection 20, which is obtained at the former step S10, so as to improve the validity and stability of the solution.

Afterward, the boundary condition and uniformity condition for the inverse operation are set on the basis of the initial environmental information obtained in step S10, which contains the geometry boundary information of the liquid article 20. The space shape of the liquid articles 20 can be expressed as a bounded function. The geometry boundary information of the liquid articles 20 can be determined by the above X-ray radiographic technology or X-ray scan imaging technology, thereby the valid active region $\Omega$ can be defined, which is $f_i=0$, for $i \notin \Omega$. The introduction of the boundary condition can speed up the solution, and to some extent ameliorate its ill-condition. Secondly, as the target object of the detection system is the liquid part, the scanned object can be divided into two parts, i.e. the liquid region $\Omega_l$ and the non-liquid region $\Omega_n$. For the uniformity of the liquid part, $f_i$=smooth function, for $i \in \Omega_l$, will be obtained. The smooth function is characterized by that both the whole variance in the liquid region $\Omega_l$ and the local fluctuation in the non-liquid region $\Omega_n$ are limited. The use of the liquid articles' uniformity greatly optimizes the extraction of the liquid article information, and improves the robustness of the system.

It is to be noted that the liquid articles having uniformity denotes those solutions, suspending liquids or emulsions that attenuate the radiations uniformly. For example, in the above sense, the milk and the porridge etc are also liquid articles of uniformity, namely, the uniformity of these liquid articles will be exhibited when they attenuate the radiations.

Therefore, with the geometry boundary condition of the liquid articles 20 being the boundary condition and the uniformity of the liquid articles being the condition of convergence, using the above formula (2), the computer data processor 60 computes to get the radiation attenuation coefficient of the liquid article 20. The valid radiation attenuation coefficient of the liquid articles then can be worked out on the basis of the obtained statistical characteristics of the pixels within the region $\Omega_l$. Thereafter, the radiation attenuation coefficient is converted into a CT value of the attenuation coefficient relative to that of water according to the above formula (1) by the computer data processor 60.

Thereafter, at step S13, the computer data processor 60 retrieves for relevant reference CT value in the database by using the identification information of the liquid articles inputted at step S10, such as 40% rum and the shape of the container.

At step S14, whether there are drugs concealed in the liquid articles can be determined by comparing the calculated CT value with the CT value of known liquid articles in the database. For example, the relative CT value of 40% rum with no drugs is 20, while the relative attenuation value of 40% rum with drugs is 22, and the predefined threshold value is 2, then 22-20>=2, so it is concluded that there are drugs concealed in the article articles. Afterwards, the identification information of the detected liquid article will be shown on the display device 67 or directly printed out.

At the above step S12, the Bayesian method can be adopted to compute the radiation attenuation coefficient of the liquid article 20 with the geometry boundary information and the uniformity as conditions. Also the non-statistical method can be adopted, wherein first solve the above formula (2) to obtain a preliminary radiation attenuation coefficient, then after optimizing using the boundary condition and uniformity, estimate the linear attenuation coefficient of the liquid article 20 on the basis of distribution of $f_i$, for $i \in \Omega_l$, to improve the validity and the stability of the computation. The computation of the radiation attenuation coefficient with the Bayesian method and the non-statistical method will be described below as examples.

[An Example of Computation of the Linear Attenuation Coefficient of Liquid Article with the Bayesian Method]

1. Determine the target function:

$$\Phi(f) = \Phi_f(g;f) + \lambda P(f) \quad (3)$$

wherein $\Phi_i(g; f)$ is a likelihood function determined by the noise characteristics of the collected data; P(f) is the metric of the uniformity for $f_i \in \Omega_l$, e.g. $P(f)=-variance(f)|_{f \in \Omega_l}$, $\lambda$ is a regulation parameter preset empirically;

2. Solve $\hat{f}=arg\ max[\Phi(f)]$ using the numerical optimization method. During the process of solution, keep $f_i=0$, for $i \notin \Omega$;

3. Calculate the probability distribution $p(\mu_{liquid})$ of $f \in \Omega_l$ to get the linear attenuation coefficient of the liquid article, e.g. $\mu_{liquid}=mean(f)|_{f \in \Omega_l}$ or $\mu_{liquid}=arg\ max(p(f))|_{f \in \Omega_l}$.

[An Example of Computation of the Linear Attenuation Coefficient of Liquid Article with the Non-Statistic Method]

1. Acquire a preliminary estimate of the radiation attenuation coefficient f by an analytic method, e.g. filter-back-projection reconstructing method or ART method;

2. Compute the uniformity of $f_i \in \Omega_l$
  a) If the preset uniformity demand is satisfied, say, the local variance is lower than a certain threshold, then acquire the attenuation coefficient of the liquid article on the basis of the statistical characteristics of $f \in \Omega_l$, such as $\mu_{liquid}=mean(f)|_{f \in \Omega_l}$.
  b) If the uniformity demand is not satisfied, then conduct a boundary condition processing and a smoothing processing with regard to the radiation attenuation coefficient f to acquire f'. Compare the orthographic projection of the processed f with the collected data g, analyze the difference between again to reconstruct and modify f, and then return step 2.

During the implementation of the non-statistical method, the operational speed and precision can be adjusted by setting different uniformity demands. In some extreme cases, the attenuation coefficient of liquid article can be obtained just by one step, without iteration.

In the case of the non-statistical method, information on the container can be calculated from the reconstructed attenuation image without using X radiographic technology to obtain the geometry boundary information of the liquid articles. Here, the information on the container is for example linear attenuation coefficients of the container, the radius of the container, the thickness of the container, and the shape of the container. The average linear attenuation of all the container pixels in the CT image is calculated as the linear attenuation coefficient of the container. The position coordinates of each container pixel are recorded, and the average wall thickness of the container and the distances from the points on the container wall to the container center are calculated based on the position coordinates. The average value of the distances from points on the container wall to the container center is calculated as the radius of the container, and the variance of the distances from the points on the container wall to the container center is used to present the container shape, for the magnitude of the variance presents the extent of the container shape deviating from standard circle, the variance is 0 when the container is a standard circle, whereas the variance is larger when the container is abnormal.

In this embodiment of the invention, the scanning is implemented by rotating the liquid article 20. By means of scanning, both the volume and the cost of the device are reduced. However, another manner of scanning, that the detected liquid article 20 stays still while the radiation source 10 with the detection and collection appliance 40 rotates, can also be adopted.

Besides, the radiation source 10 may comprise one or more X-ray machines, as well as one or more isotope sources, and the radiation energy of the X-ray machines is adjustable. In the case that the radiation source 10 comprises a plurality of X-ray machines or isotope sources, there may be the same number of detectors as the X-ray machines or isotope sources, and these X-ray machines or isotope sources are set correspondingly. Herein, the detectors may be gas detectors, liquid detectors, solid detectors or semiconductor detectors, and may have an energy switching function. Besides, the detectors can work under the mode of one-dimensional array or two-dimensional arrays, i.e. the line array detector or the area array detector.

Figure 4:
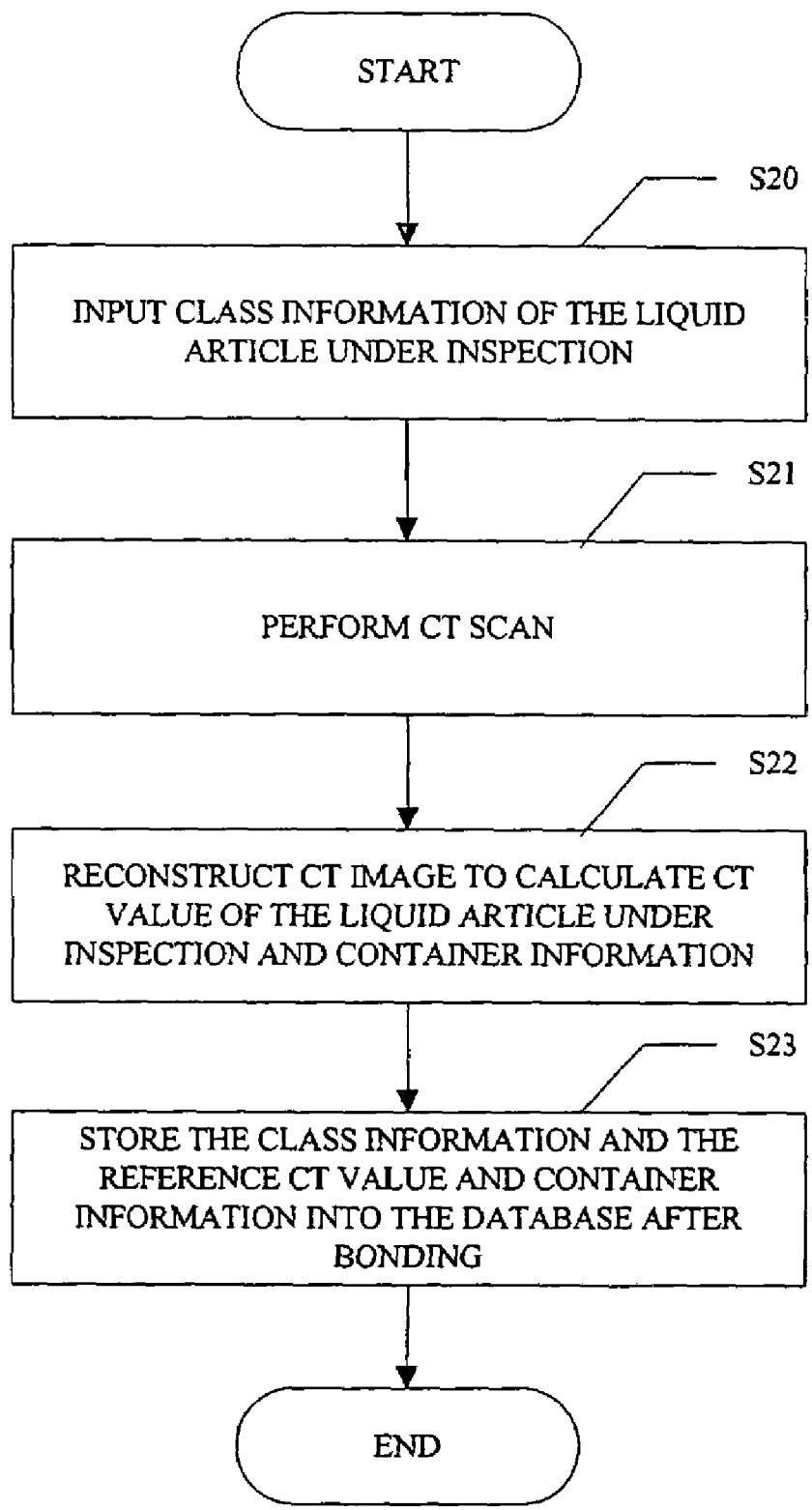
FIG. 4 shows a detailed flow chart of the process for expanding the database.

According to an embodiment of the invention, users can expand the database as required, for example, when the attribute information of a new type of liquid articles is needed to be added into the database. FIG. 4 shows a detailed flow chart of the process for expanding the database.

At step S20, the operator powers the system. The system is ready after self-check, and logs onto the setting interface of the database. The operator inputs the identification of the liquid articles required to be added into the database (main classes, subclasses and remarks), such as the main class is rum, the subclass is 40%, and the remark states coming from Brazil.

At step S21, the operator places liquid samples onto the stage 30 and presses the scan button. And then the system performs the above CT scan to obtain projection values of various angles.

At step S22, the computer data processor 60 conducts CT image reconstruction in the manner said above, to get the CT value of the liquid articles and container information from the reconstructed CT image.

At step S23, the identification of the liquid articles, the reference CT value and container information are stored in the database after bonding together.

If the operator desires to further expand other samples, then the same operations as above are performed to other samples. Otherwise, the operator exits the setting interface of the database, and the expanding process ends.

Figure 5:
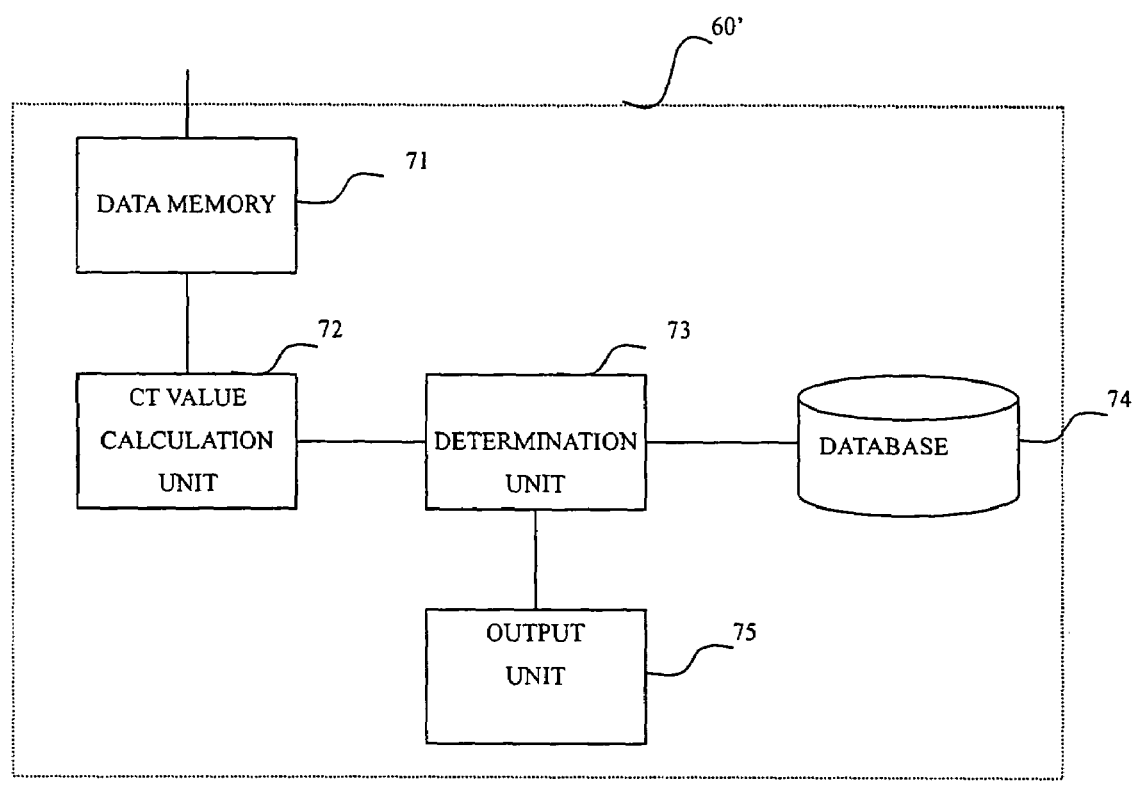
FIG. 5 shows a functional block diagram of the computer data processor in the inspection device of FIG. 1.

The computation procedure of the radiation attenuation coefficient and the acquiring procedure of the CT value of the liquid article 20 are described above in the form that the computer data processor 60 runs the programs containing the predetermined data processing algorithm. However, the computer data processor 60 may be embodied in other forms. FIG. 5 is a functional block diagram of the computer data processor 60 of the inspection device of FIG. 1.

As shown in FIG. 5, as another example of the computer data processor, this computer data processor 60' comprises the following: a data memory 71, which stores the original environment information and the multi-angle projection data and etc, such as the system matrices $H_1, \ldots H_M$ to describe the system property; the database 74, which stores the CT values of various liquid articles and container information to be used for the retrieval and comparison of the detecting procedure; a CT value calculation unit 72, which calculates the radiation attenuation coefficient of the detected liquid article 20 based on the above formula (2), under the condition of uniformity of the liquid article, on the basis of the initial environmental information stored in the data memory 71 such as the geometry boundary information of liquid article, and the multi-angle projection data, and converts the radiation attenuation coefficient into a CT value; a determination unit 73, which compares the CT value of the detected liquid article 20 computed by the CT value computing unit 72 with a reference CT value of corresponding type of liquid article stored in the database, and determines that there may be drugs concealed in the detected liquid article 20 when the difference therebetween is larger than a predefined threshold value; a output unit 75 such as a display or other output device, for presenting the conclusion acquired by the determination unit 73 to the operator.

Although exemplary embodiments of the present invention have been described hereinabove, it should be clear to those skilled in the field that any variations and/or modifications of the basic inventive concepts will still fall within the scope of the present invention, as defined in the appended claims.

What is claimed is:

1. A method for inspection of a liquid article to determine a presence of drugs concealed in said liquid article, comprising the steps of:
    emitting radiation beams having a single energy and transmitting said single energy beams through the liquid article;
    receiving, at a detection and collection apparatus, the single-energy radiation beams transmitted through the liquid article to get multi-angle projection data;
    inversely operating the multi-angle projection data based on uniformity of the liquid article, using a computer data processor, to obtain a calculated attribute value of the liquid article under inspection;
    retrieving, by the computer data processor, a reference attribute value in a pre-created database by using the identification information of the liquid article as an index, and calculating a difference between the calculated attribute value and the reference attribute value;
    determining whether the difference is larger than a predefined threshold value to obtain a result; and
    outputting the result to a user to indicate that there are drugs concealed in the liquid article when the difference is determined to be larger than the predefined threshold value.

2. The method of claim 1, wherein the calculated attribute value is a linear attenuation coefficient.

3. The method of claim 2, wherein the calculated attribute value is a relative linear attenuation coefficient.

4. The method of claim 3, wherein the relative linear attenuation coefficient attribute value is calculated as follows:

$$CT = \frac{\mu_{CALCULATION} - \mu_{WATER}}{\mu_{WATER}} \times 1000$$

wherein $\mu_{WATER}$ denotes a linear attenuation coefficient of water, and $\mu_{CALCULATION}$ denotes the calculated linear attenuation coefficient.

5. The method of claim 2, wherein the identification information includes at least one of name, class, container information and producing area of the liquid article.

6. The method of claim 5, further comprising the steps of:
    forming an image of the liquid article by using the linear attenuation coefficient of various points on the liquid article; and
    calculating the container information based on the image.

7. The method of claim 1, wherein the database is expandable.

8. The method of claim 1, further comprising a step of:
    acquiring initial environmental information;
    wherein the attribute value of the liquid article is calculated by inversely operating the multi-angle projection data based on the initial environmental information and the uniformity of the liquid article.

9. The method of claim 8, wherein the initial environmental information includes geometry boundary information of the liquid article.

10. The method of claim 9, wherein the geometry boundary information is obtained by the radiographic technology or the scan imaging technology.

11. A device for inspection of a liquid article to determine a presence of drugs concealed in said liquid article, comprising:
    a radiation source configured to emit radiation beams having a single energy and to transmit said single energy beams through the liquid article;
    a detection and collection appliance configured to receive the single-energy radiation beams transmitted through the liquid article to get multi-angle projection data; and
    a computer data processor comprising:
        a calculation unit for inversely operating the multi-angle projection data based on a uniformity of the liquid article to obtain a calculated attribute value of the liquid article;
        a determination unit for retrieving a reference attribute value in a pre-created database setup by using identification information of the liquid article as an index, and calculating a difference between the calculated attribute value and the reference attribute value; and
        said determination unit determining whether the difference is larger than a predefined threshold value to obtain a result; and
    an output unit for outputting the result to a user indicating that there are drugs concealed in the liquid article when the difference is determined to be larger than the predefined threshold value.

12. The device of claim 11, wherein the calculated attribute value is a linear attenuation coefficient.

13. The device of claim 12, wherein the calculated attribute value is a relative linear attenuation coefficient.

14. The device of claim 13, wherein the relative linear attenuation coefficient attribute value is calculated as follows:

$$CT = \frac{\mu_{CALCULATION} - \mu_{WATER}}{\mu_{WATER}} \times 1000$$

wherein $\mu_{WATER}$ denotes a linear attenuation coefficient of water, and $\mu_{CALCULATION}$ denotes the calculated linear attenuation coefficient.

15. The device of claim 11, wherein the identification information includes at least one of name, class, container information and producing area of the liquid article under inspection.

16. The device of claim 15, wherein the computer data processor is further configured to form an image of the liquid article under inspection by using the linear attenuation coefficient of various points on the inspected liquid article and calculate the container information based on the image.

17. The device of claim 11, wherein the database is expandable.

18. The device of claim 11, wherein the detection and collection appliance acquires initial environmental information, the attribute value of the inspected liquid article is calculated by inversely operating the multi-angle projection data based on the initial environmental information and the uniformity of the liquid article.

19. The device of claim 18, wherein the initial environmental information includes geometry boundary information of the liquid article.

20. The device of claim 19, wherein the geometry boundary information is obtained by the radiographic technology or the scan imaging technology.

* * * * *